United States Patent
Palma et al.

(10) Patent No.: US 6,629,930 B2
(45) Date of Patent: Oct. 7, 2003

(54) PRESSURE HOLTER THAT IS SELF-PROGRAMMABLE AS A FUNCTION OF THE MONITORED PHYSICAL ACTIVITY OF THE PATIENT

(75) Inventors: Giuseppe Palma, Crema (IT); Leonardo Dino Avella, Crema (IT); Antonino Cucé, Crema (IT); Davide Platania, Crema (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 181 days.

(21) Appl. No.: 09/825,157

(22) Filed: Apr. 3, 2001

(65) Prior Publication Data

US 2002/0002338 A1 Jan. 3, 2002

(30) Foreign Application Priority Data

Apr. 4, 2000 (EP) .............................. 00830252

(51) Int. Cl.⁷ .............................. A61B 5/02; G06F 17/00
(52) U.S. Cl. .................. 600/485; 128/925; 600/490; 600/500
(58) Field of Search ................. 600/300, 301, 600/481, 485, 490, 493, 494, 495, 496, 500, 503, 504, 595; 128/897, 898, 900, 920, 923, 924, 925

(56) References Cited

U.S. PATENT DOCUMENTS 6,160,478 A * 12/2000 Jacobsen et al. ............ 600/300
6,179,782 B1 * 1/2001 Cuce ....................... 600/481
6,471,655 B1 * 10/2002 Baura ...................... 600/485
6,514,211 B1 * 2/2003 Baura ...................... 600/490

FOREIGN PATENT DOCUMENTS

| DE | 19832361 | 2/2000 |
|---|---|---|
| EP | 0917069 | 5/1999 |
| EP | 0967554 | 12/1999 |
| EP | 967554 A1 * | 12/1999 |
| EP | 1142531 A1 * | 10/2001 |
| WO | 93/16636 | 9/1993 |

OTHER PUBLICATIONS

Patent Abstracts of Japan, vol. 017, No. 638 (C–1133), Nov. 26, 1993 & JP 05 200004 A (Matsushita Electric Works Ltd), Aug. 10, 1993.

* cited by examiner

Primary Examiner—Willis R. Wolfe
(74) Attorney, Agent, or Firm—Lisa K. Jorgenson; Allen, Dyer, Doppelt, Milbrath & Gilchrist, P.A.

(57) ABSTRACT

A blood pressure Holter system includes a pneumatic constriction sleeve to be worn on an arm of the user and includes a first sensor for acquiring systolic and diastolic values of arterial pressure of the user. A second sensor is carried adjacent a chest of the user for sensing movement of the user's body. The system further includes a detection and classification circuit for detecting and classifying movement of the user's body for producing an index of a state of physical exertion corresponding to systolic and diastolic values of arterial pressure. A fuzzy logic controller processes the systolic and diastolic values of arterial pressure using fuzzy logic.

27 Claims, 10 Drawing Sheets

PRESSURE HOLTER THAT IS SELF-PROGRAMMABLE AS A FUNCTION OF THE MONITORED PHYSICAL ACTIVITY OF THE PATIENT

FIELD OF THE INVENTION

The invention relates in general to noninvasive methods and instruments for measuring blood pressure, and in particular, to an automatic sphygmomanometer worn by a patient for monitoring blood pressure during prolonged periods while conducting normal daily activities.

BACKGROUND OF THE INVENTION

Blood pressure is subject to continuous variations tied to several factors including age, sex, environment, season, temperature, altitude and the like. Moreover, blood pressure of a subject may vary during the day because of many contingent factors including posture, respiration, and the state of muscular and/or cerebral activity. In particular, physical exertion may cause large increases in blood pressure.

Significant variations of blood pressure due to other factors than those noted above may indicate that the circulatory system and/or the heart is malfunctioning. For these reasons, it is useful to check the blood pressure throughout the entire day to study the magnitude of the variations and the presence of possible anomalies.

For these reasons, so-called pressure Holters are widely used. These portable instruments are automatic sphygmomanometers that are easy to use and are of minimum size which, when worn by the patient, measures the blood pressure at preset intervals of time. A limitation of these portable instruments is primarily tied to the difficulty of associating the measured value of blood pressure to the current conditions of the patient at the time of the measurement.

Not knowing the actual conditions at the time of measurement, the recorded reading may be wrongly interpreted and it is very difficult to find out and recognize the magnitude of these errors. It is evident that there is a need and/or utility for a blood pressure Holter capable of assessing the conditions that may influence the measured values of blood pressure, and in particular, the state of physical exertion of the patient because of the strong influence that it has on arterial pressure.

SUMMARY OF THE INVENTION

An object of the invention is to provide an intelligent instrument that is more reliable in terms of the data it provides, and moreover, is capable of automatically managing the measurement operations.

According to the present invention, a blood pressure Holter system includes a system of classification of the current state of physical exertion as detected by one or more movement sensors, and is based on a fuzzy logic possessing according to predefined algorithms.

According to another important aspect of the blood pressure Holter system, the inflating/deflating of the constricting pneumatic sleeve as well as the processing of the signals generated by the pressure sensor for calculating the maximum and minimum arterial pressures are coordinated by the on-board fuzzy logic microcontroller. In this way, the inflating of the sleeve is less traumatic for the patient while the determination of the maximum and minimum values of the blood pressure is carried out in a substantially identical manner as a doctor would do manually. This is by virtue of the intrinsic peculiarity of controlling the inflating/deflating of the sleeve, and of processing the pressure signal carried out according to a fuzzy logic algorithm.

Besides correlating the blood pressure measurements with corresponding evaluation data on the state of exertion of the patient at the moment of the measurement, the instrument may optionally self-program itself by exploiting the information on the current physical activity even to time the carrying out of new pressure measurements.

For example, to avoid spurious measurements if the patient is doing a particularly intense physical activity, a scheduled measurement may be automatically postponed by the Holter system. In contrast, by checking the results of most recent blood pressure readings, if anomalies are detected, the Holter system may automatically decide to increase the frequency of measurements.

DETAILED DESCRIPTION OF THE PREFERRED EMBODIMENTS

Figure 1:
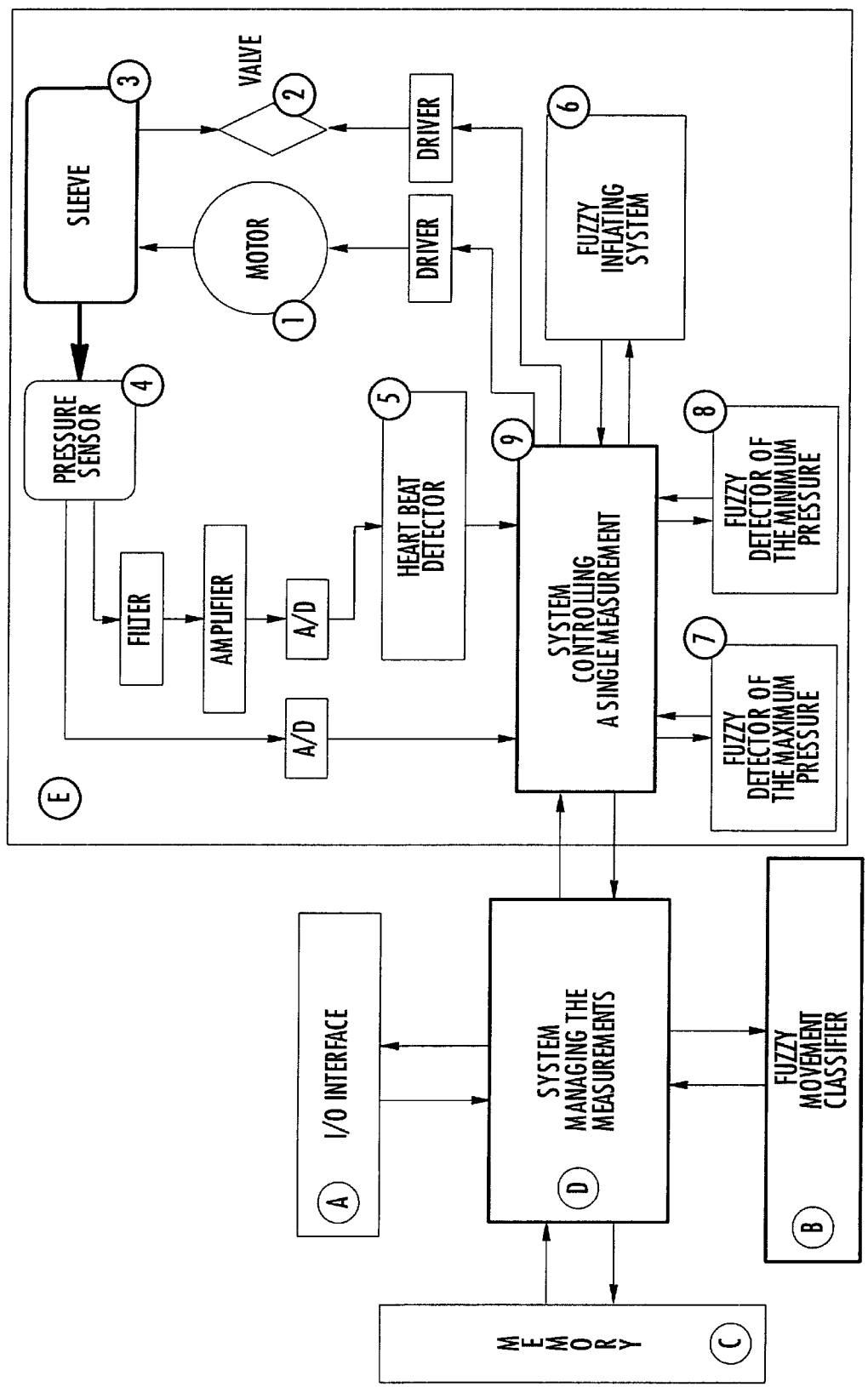
FIG. 1 is a functional block diagram of a blood pressure Holter according to the present invention.

The functional block diagram of the instrument of the invention is shown in FIG. 1. The instrument includes five main functional blocks. The I/O interface (block A) of the system permits the introduction of the data necessary for managing the measurement, and for making available external the system the recorded results provided by the Holter system. For example, the interface may include a keyboard for introducing data and for accessing a selection menu, a display for visualizing the measurement results, and a communication port with an external PC, and the like.

The function of detecting and classifying the movement of the patient is performed by block B. This is done by processing, according to a predefined fuzzy logic algorithm, information on the movements of one or more parts of the body of the patient. Movement is detected by respective sensors worn by the patient. This subsystem provides for a global classification of the state of physical exertion of the patient at a certain time.

The memory (block C) of the system stores all information necessary to manage the measurements, as well as the readings and results produced by the instrument. For example, it contains data relative to the patient, such as age, sex, and eventually average values of minimum and maximum blood pressure as measured by the doctor. Data also includes the monitoring program which determines the frequency with which readings are taken, delay and/or anticipation of taking the readings depending on the assessed state of physical exertion, and/or detection of anomalies of the pressure values with respect to recorded average values. The pressure readings, indexes of the state of physical exertion, and the like are also part of the data.

The control system for taking the measurements is represented by block D. It provides for coordinately activating the different parts of the Holter, writes in a dedicated buffer of the memory the results obtained, and processes the results for establishing when to perform the next measurement. For example, upon detecting anomalies, the system may decide to increase the frequency of measurements. Parameters for the management of measurements, in particular, the base frequency of measurements and the intervals of anticipation and/or posticipation of measurements, may be programmed by the doctor.

The single blood pressure measurements are performed by block E. Its principle of operation is based on the indirect oscillometric method of measurement. The blood pressure signal is detected by a sensor and the arterial beats are derived by processing the pressure signal. The fuzzy logic manages the inflation and the deflation of the pneumatic constriction sleeve as well as carrying out the evaluation of the maximum and minimum blood pressure values. Block E includes the following parts.

The motor drive pump (1) forces air into the constriction sleeve (4). The motor is controlled by a driving circuit (driver) which in turn is controlled by the control system (9) that establishes when and with which power air must be pumped. The valve (2) permits the release of compressed air out of the sleeve. The relative driver circuit (driver) regulates the opening and closing of the valve under control of the control system (9).

The constriction sleeve (3) is a flexible tube functionally placed around an arm of the patient. It is inflated until its internal pressure exceeds the maximum arterial pressure. During the phase of deflation, the maximum and minimum arterial pressures coincide with the internal pressure of the air in the sleeve, respectively in coincidence of the instant at which a first arterial tone appears and disappears.

Figure 2:
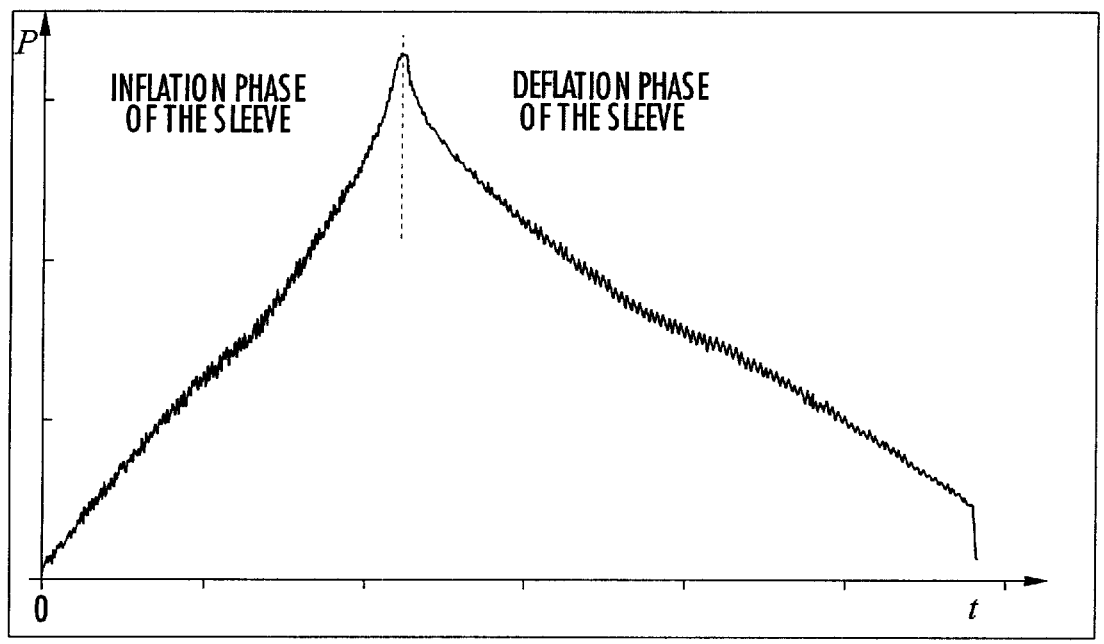
FIG. 2 is a timing diagram of a typical pressure signal detected during a measurement using the device according to the present invention.

The pressure sensor (4) detects the internal pressure of the air into the sleeve. The generated pressure signal, an example of which is shown in FIG. 2, has of course an increasing trend during a phase of inflation of the sleeve and a decreasing trend during a phase of deflation of the sleeve. Moreover, a periodic component of relatively small amplitude is present, which is due to the arterial pulsations during the systolic and diastolic phases. These pulsations, because of the direct contact of the sleeve with the arm, cause small variations of the internal pressure of the sleeve. Therefore, these oscillations reflect the heart pulsations. Even the frequency of these oscillations coincides with the frequency of the heart beat.

The heart beat detector (5) is implemented via an algorithm that extracts from the pressure signal the component relative to the arterial pulsations by identifying, in particular, their amplitude and frequency. This information is crucial to establish the maximum and minimum values of arterial pressure.

The fuzzy control of inflation (6) is also implemented via a fuzzy logic algorithm. Based on the parameters relative to the internal air pressure of the sleeve and to the arterial pulsations, the fuzzy control provides to the control system (9) the parameters necessary for regulating the inflation. Of course, the sleeve must be inflated until its internal pressure exceeds the maximum arterial pressure. However, to minimize the discomfort caused to the patient, the system automatically avoids inflating the sleeve beyond what is necessary. Therefore, fuzzy logic rules are structured in such a way that, upon approaching by the internal pressure of the sleeve the maximum arterial pressure, the rate of air insufflation into the sleeve is gradually decreased.

The maximum pressure fuzzy detection (7) is provided by a fuzzy logic algorithm for detection of the maximum pressure. The measurement of the maximum arterial pressure takes place during the phase of deflation of the sleeve. During the release of the internal pressure of the sleeve, the fuzzy logic circuitry receives input parameters relative to the amplitude of the arterial pulsations. Based upon a predefined set of fuzzy rules, the fuzzy controller dynamically processes the input parameters and outputs a parameter representative of the degree of approximation of the internal pressure of the sleeve to the maximum arterial pressure.

The fuzzy assessment of minimum pressure (8) is provided by a fuzzy algorithm for assessing the minimum arterial pressure. The measurement of the minimum arterial pressure takes place during the phase of deflation of the sleeve. The fuzzy algorithm dynamically processes parameters relative to the arterial pulsations and, upon gradually releasing the pressure from the sleeve, outputs a parameter representative of the degree of approximation of the internal pressure of the sleeve to the minimum arterial pressure.

The control system of the single test (9) is the heart of the pressure Holter. It coordinates the functioning of all the different parts. It receives the electrical signals relative to the internal pressure of the sleeve and to the heart beats. It processes this information producing parameters to be input to the distinct control and fuzzy logic processing systems. As a function of the results provided by the different fuzzy logic systems, it controls the motors of the air pump and of the release valve. Moreover, it communicates with the central control system of the instrument by transferring the results obtained by the blood pressure measuring device, and receives back the command for initiating the tests.

Figure 3:
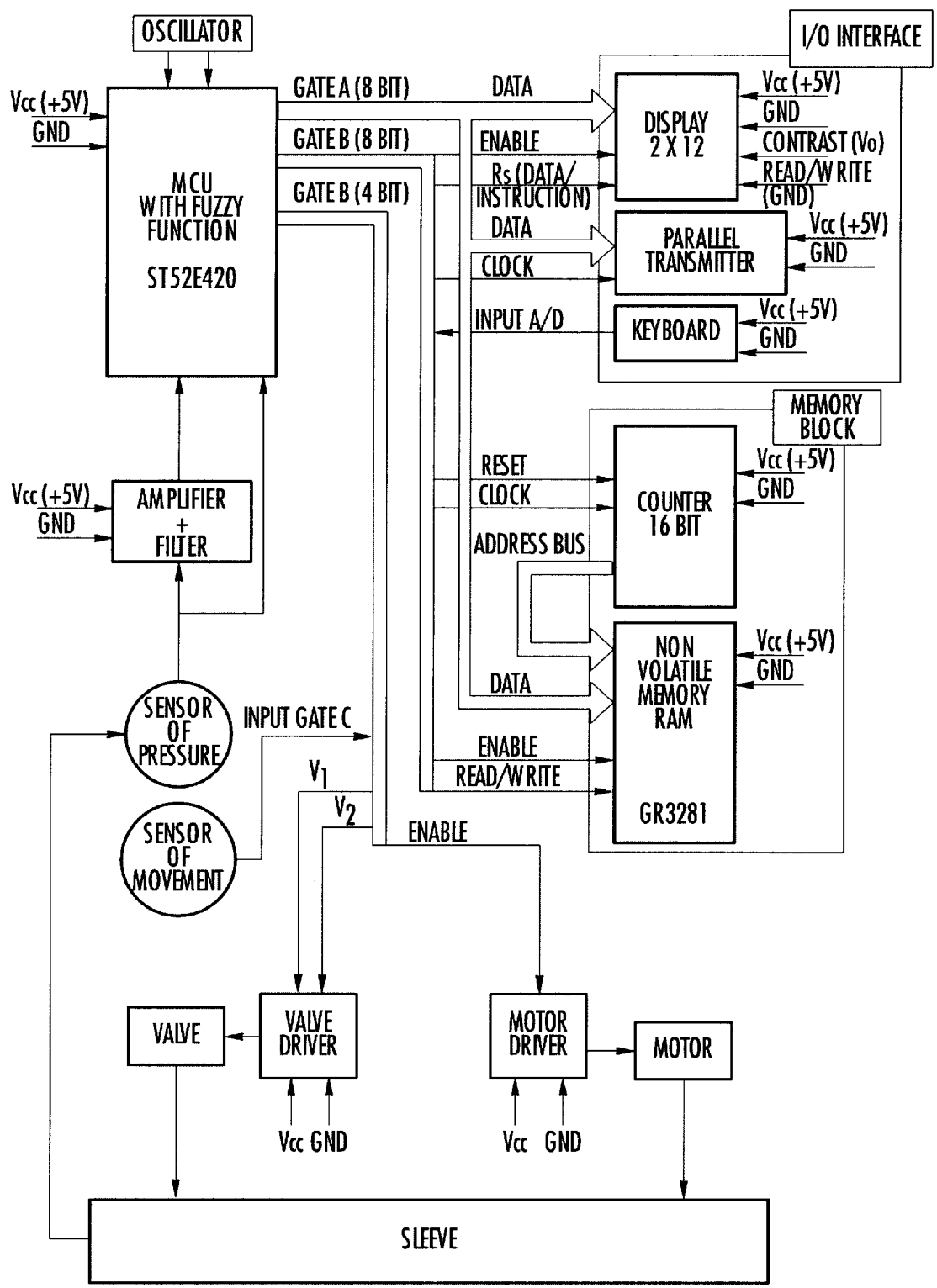
FIG. 3 is an architectural scheme of the device according to the present invention.

A scheme of operation of an instrument made according to the present invention is depicted in FIG. 3. The Holter is composed of an inflatable sleeve to be wound around the right arm of the patient. By virtue of the motor driven pump, air is pumped inside the sleeve and by way of the release valve, air can exit. The motor has two states: active or disabled. The valve may be commanded in different conditions: fully open, closed, and half open. The motor and the valve actuator are driven by respective driving circuits. Two sensors are used: one laced on the bust or chest of the patient to detect movements of the trunk and the other sensor senses the internal air pressure of the sleeve.

The electrical signal produced by the pressure sensor propagates along two paths. A first path reaches directly an analog/digital input gate of the controller and its function is to provide to the controller data on the internal pressure of the sleeve. The same signal is used also for classifying the movement of the arm. In fact, on the base of the disturbances that a movement of the arm causes on the pressure signal, it is possible to quantify the intensity of the arm movement. The second path includes an active filter with a low frequency cut-off frequency in the vicinity of 0.7 Hz and a gain of about 150, and leads to an analog/digital input gate of the controller.

Figure 4:
FIG. 4 is a plot showing the pressure variations corresponding to heart pulsations detected by the device according to the present invention.

The signal that is obtained after processing is shown in FIG. 4. The oscillations coincide with the arterial pulsations. The I/O interface is composed of the following. First, a four-key keyboard is provided. One key for accessing a selection menu, two keys for scrolling through the menu, and one key for selecting. Through the same keyboard, the frequency at which the blood pressure tests must be performed may be programmed.

Second, a monitor is provided for displaying the menu options and the results of a test. In particular, the assessed minimum and maximum values of the arterial pressure and the parameter of classification of the state of physical exertion at the time of the blood pressure tests are displayed. Third, a communication parallel port is provided for downloading the stored results of the measurements on a personal computer (PC). That is, the pressure values as well as the minimum and maximum blood pressure and physical activity data, recorded during a full day, are downloaded.

The internal RAM of the instrument permits storage of the results of the measurements and the pressure readings accumulated during a full day. Moreover, in the RAM are stored the variables that are needed for carrying out the tests under fuzzy logic control.

The fuzzy microcontroller ST52E420 performs the following functions. First, all the external input signals are acquired through the analog/digital input ports. That is, the pressure and movement signals as detected by the respective sensors, as well as the input parameters that are conveyed through the I/O interface. Second, fuzzy logic processing is performed on the acquired parameters for managing the inflation and deflation of the sleeve, and for calculating the minimum and maximum blood pressure values. Third, fuzzy logic processing on information related to movement provided by the sensors is performed for producing a classification on the state of physical exertion of the patient. Fourth, driving of peripheral devices, in particular, the motorized pump and valve drivers and the I/O interface is performed. Finally, management of the memory, and management of the tests as a function of the results obtained during the preceding tests and of the set-up parameters stored during the programming of the instrument are performed.

Figure 5:
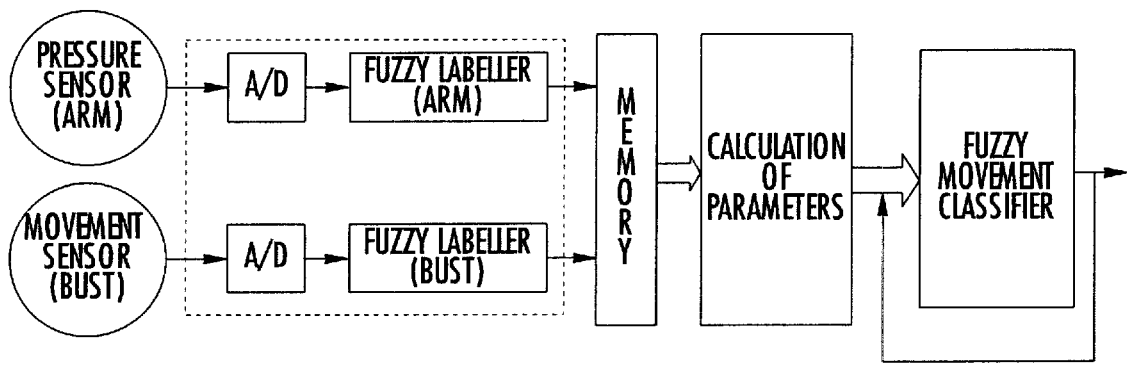
FIG. 5 is a functional block diagram of the classification system of the physical activity being carried out by the patient according to the present invention.

The movement classifier will now be described. The fuzzy logic algorithm for classifying the movement is implemented within the microcontroller. As shown in the specific functional scheme of FIG. 5, the device uses the signals provided by the two sensors, one of which is placed on the right arm of the patient and senses the internal pressure of the sleeve. The other sensor is placed on the chest and detects movement thereof.

A labeling system is associated with each sensor for effecting a first fuzzy classification of the movement of the monitored part of the body on the basis of the fluctuations that the signals output by the sensors reveal. Dynamically all the parameters of classification of the movement of the different parts of the body are stored in the RAM as illustrated in FIGS. 3 and 4. Information obtained on the movement of different parts of the body are formalized as input parameters for the fuzzy logic algorithms having a second classification level. In this way, a global classification of the movement of the patient being monitored is produced as: calm, normal and restless.

The fuzzy algorithm for inflation of the sleeve will now be discussed. The fuzzy algorithm for inflating the sleeve is implemented within the microcontroller. The fuzzy control of the inflation is such that when the pressure of the sleeve exceeds the maximum arterial pressure, the deflation phase is immediately initiated, thus avoiding to further inflate the sleeve without any purpose. This minimizes the discomfort of the patient.

Figure 6:
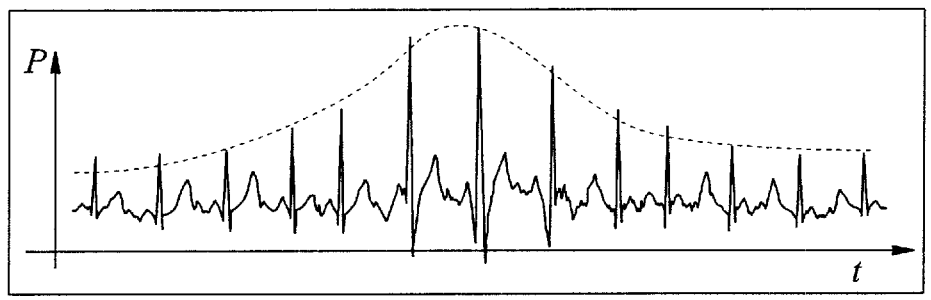
FIG. 6 is a diagram of the amplitude of arterial pulsations during an inflating phase of the constriction sleeve according to the present invention.

The inflation algorithm receives as input information on the amplitude of the arterial pulsations as a function of the point at which the internal pressure of the sleeve has exceeded the maximum arterial pressure, and therefore the deflation phase may be started. During a phase of gradual release of the internal air pressure of the sleeve, the amplitude of the pulsation follows a bell-shaped characteristic, as shown in FIG. 6. Upon overcoming the peak of the bell-shaped curve, the exceeding of the maximum arterial pressure is confirmed.

In practice, as soon as the controller commands the start of a blood pressure measurement, the system starts to inflate the sleeve. At a certain instant, the inflation stops and the amplitude of arterial pulsation is read. By performing a comparison of the read amplitude with the amplitude read before and stored in a buffer, how much the sleeve should be inflated before repeating the comparison can be established. The fuzzy rules establish the successive instant at which to compare again the current reading with the preceding one.

Therefore, at the Nth reading, the fuzzy logic processor receives the parameter $\Delta = A_N - A_{N-1}$ in terms of dimension and sign. On the basis of inference rules, the processor established the next Check Point. The rules are of the type:

IF $\Delta$ IS low AND $\Delta_{sign}$ IS positive THEN Check Point IS behind; and IF $\Delta$ IS medium AND $\Delta_{sign}$ IS positive THEN Check Point IS medium.

Figure 7:
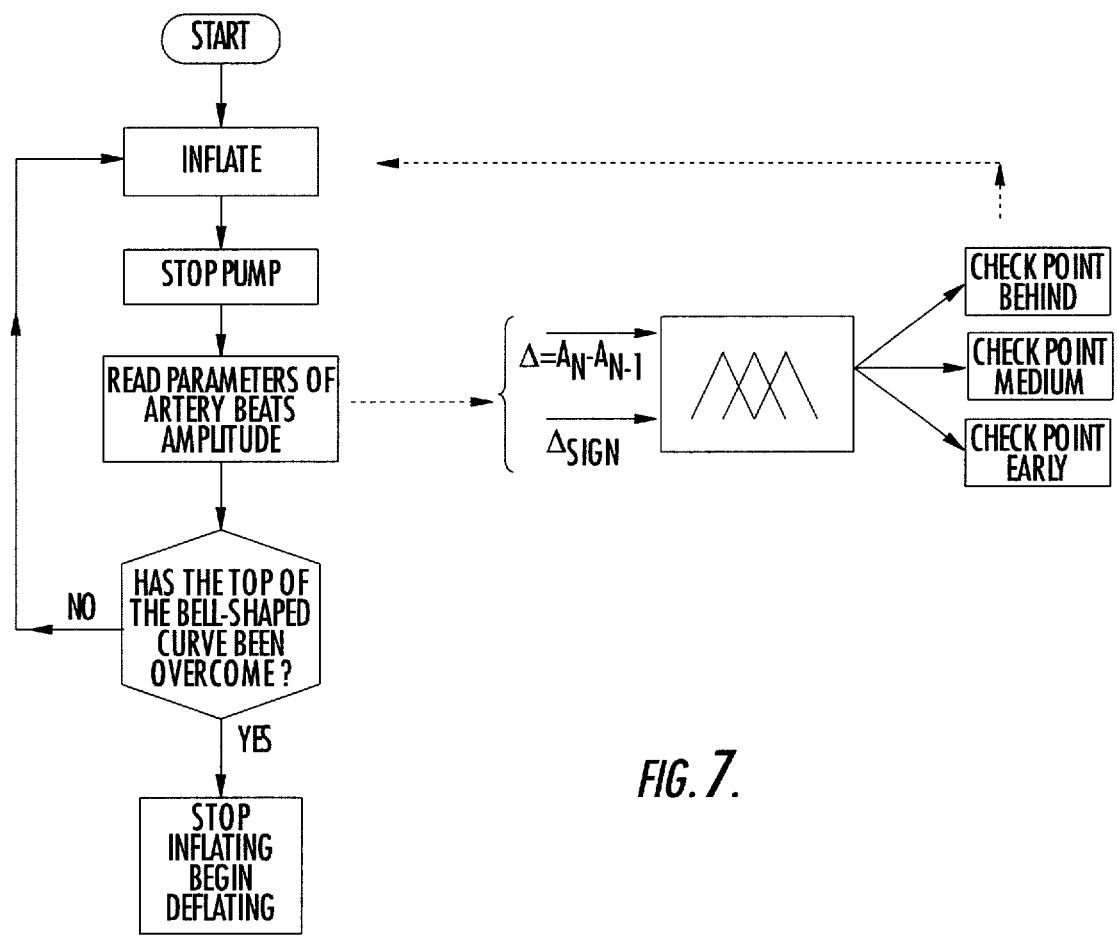
FIG. 7 is a flow chart of the algorithm for management of the inflation and deflation of the sleeve according to the present invention.

The flow chart of the measurement of the inflation/deflation of the sleeve is depicted in FIG. 7.

Figure 8:
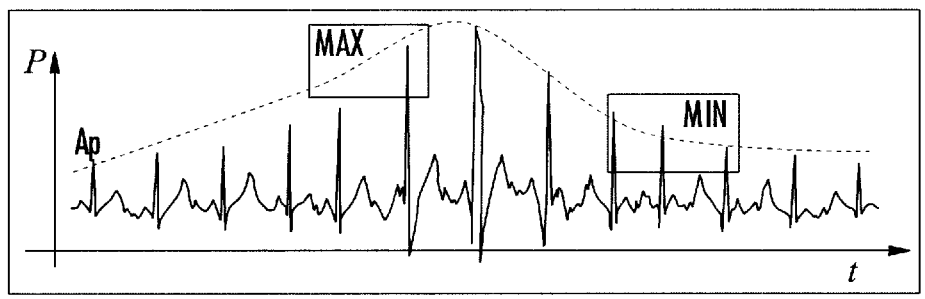
FIG. 8 is a graph showing the arterial pulsations during a phase of deflation of the constriction sleeve according to the present invention.
Figure 9:
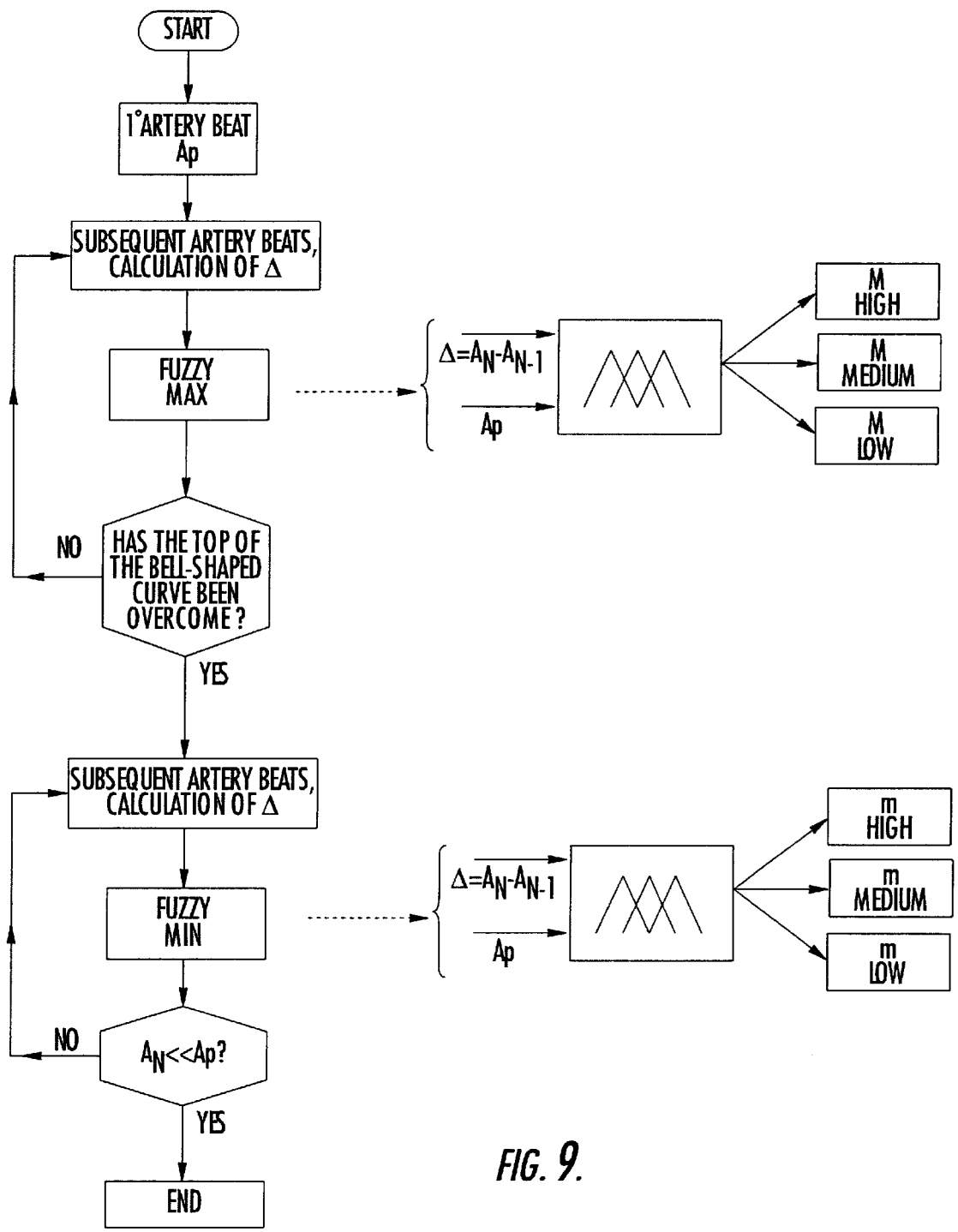
FIG. 9 is a flow chart of the algorithms for evaluation of the maximum and minimum arterial pressure according to the present invention.

The fuzzy logic algorithm for assessing the maximum pressure will now be discussed. The maximum arterial pressure is assessed during the deflation phase of the sleeve. The fuzzy algorithm for assessing the maximum pressure receives as input the parameters relative to the amplitude of the arterial pulsations. The amplitude of the arterial pulsations follows a bell-shaped characteristic, as depicted in FIG. 8. Experimentally, it is been verified that the maximum arterial pressure coincides with the zone of maximum gradient of the rising slope of the characteristic curve.

As soon as the phase of releasing the internal air pressure of the sleeve has started, and after waiting a moment for the signal to stabilize itself, the amplitude of the first pulsation Ap is read. The successive amplitudes are read and the parameter $\Delta = A_N - A_{N-1}$, where $A_N$ is the amplitude of the pulsation read at the Nth reading is evaluated. The fuzzy algorithm receives the Ap and the $\Delta$ parameters. As a function of a set of rules, it generates the M parameter representative of the degree of approximation of the internal pressure of the sleeve to the maximum arterial pressure.

The rules are structured to evaluate the gradient of rise of the bell-shaped curve as referred to the amplitude of the first beat which is a parameter strictly tied to the individual characteristic of the patient. The rules are of the following type:

IF Δ IS LOW AND Ap IS LOW, THEN M IS LOW

IF Δ IS HIGH AND Ap IS LOW, THEN M IS HIGH

The fuzzy logic algorithm for the assessment of the minimum pressure will now be discussed. The fuzzy logic algorithm for assessing the minimum arterial pressure is also implemented within the microcontroller. Even the assessment of the minimum blood pressure takes place during the phase of releasing the internal air pressure of the sleeve. The input parameters of the fuzzy algorithm are $\Delta = A_N - A_{N-1}$ and Ap which are defined above.

The fuzzy algorithm based upon a set of rules outputs a parameter m representative of the approximation of the internal air pressure of the sleeve to the minimum arterial pressure. Along the bell-shaped characteristic of FIG. 8, reflecting the evolution of the amplitude of arterial pulsations during the release of the pressure of the sleeve, the minimum arterial pressure coincides with the zone in which the decreasing gradient of the bell-shaped profile starts to stabilize itself. The fuzzy rules are of the following type:

IF Δ IS HIGH AND Ap IS LOW, THEN m IS LOW

IF Δ IS LOW AND Ap IS LOW, THEN m IS HIGH etc.

Figure 10:
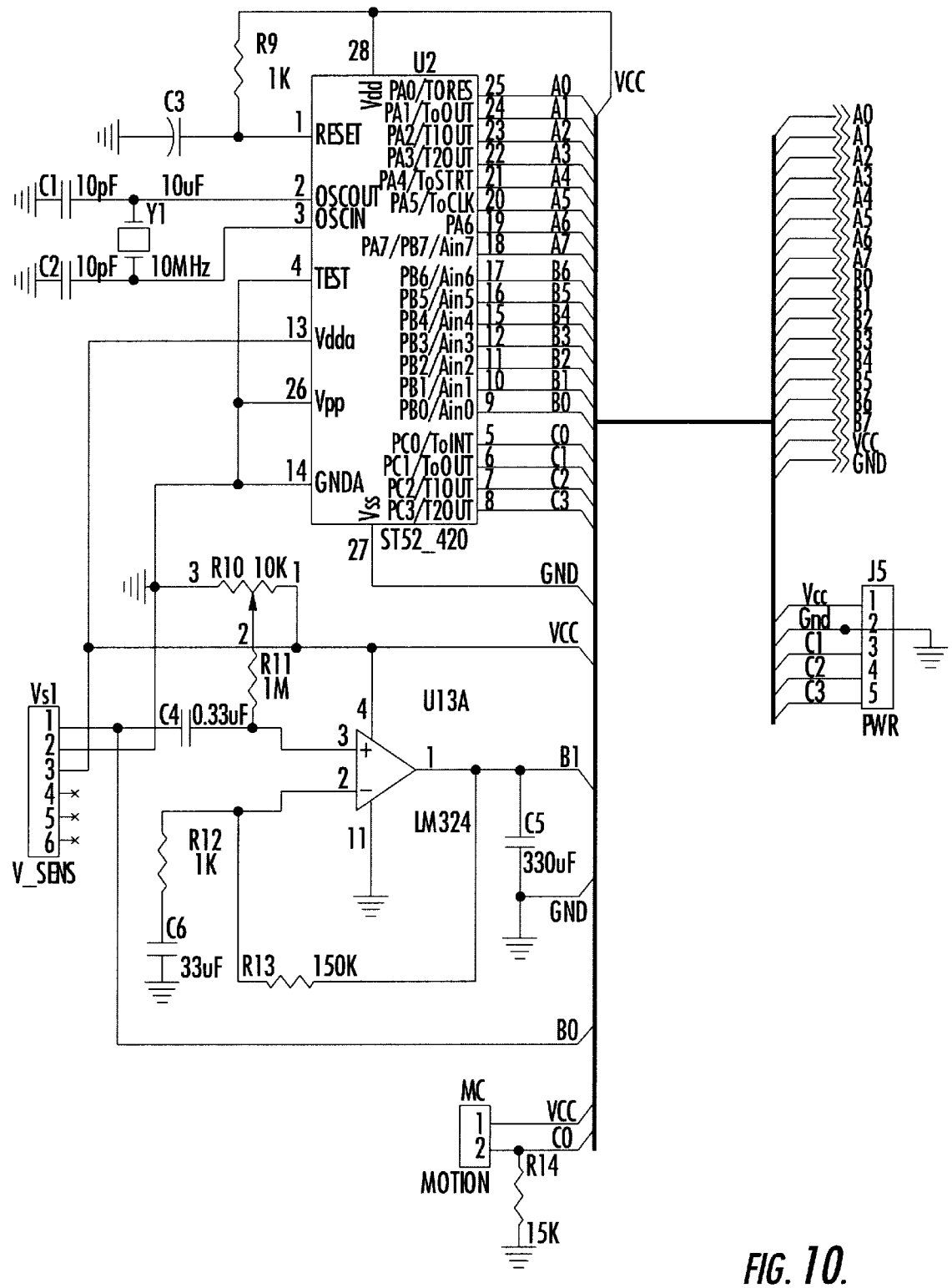
FIGS. 10–13 are electrical circuit diagrams for the respective implementations of the control, amplification and filtering unit; the memory and data transfer unit; the drive and control circuit of the motors; and the valves and interfacing keyboard and display.
Figure 11:
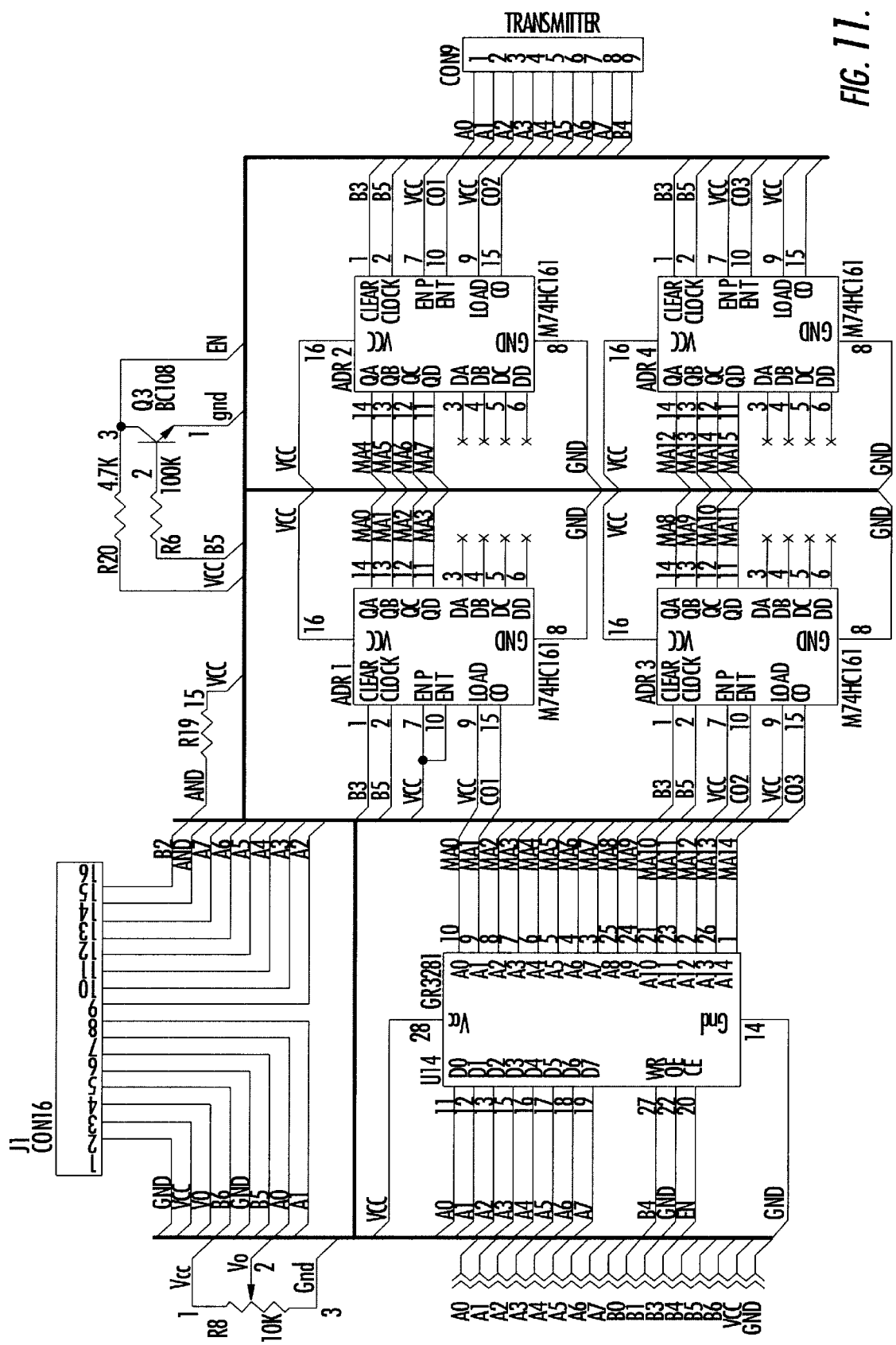
Figure 12:
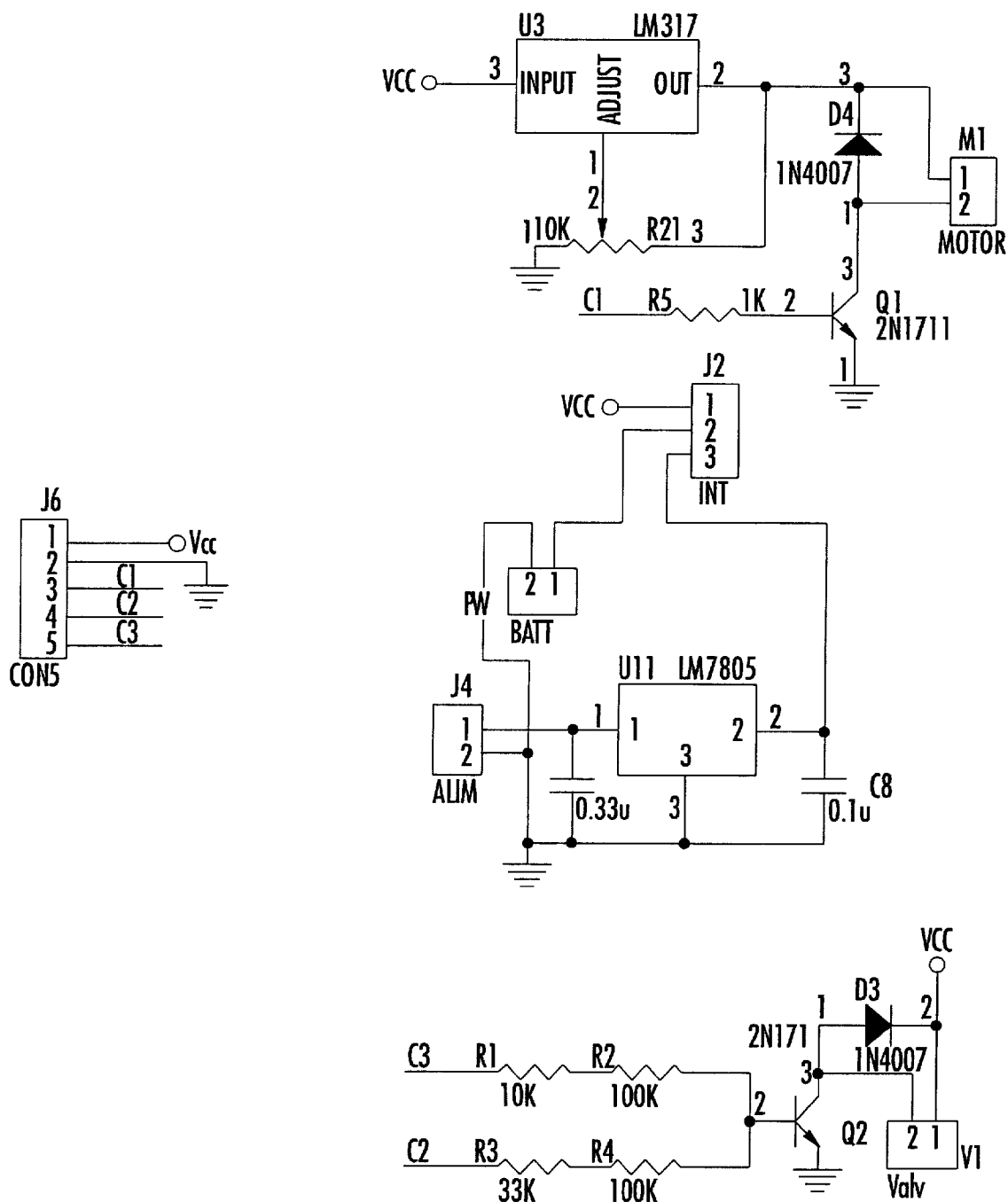
Figure 13:
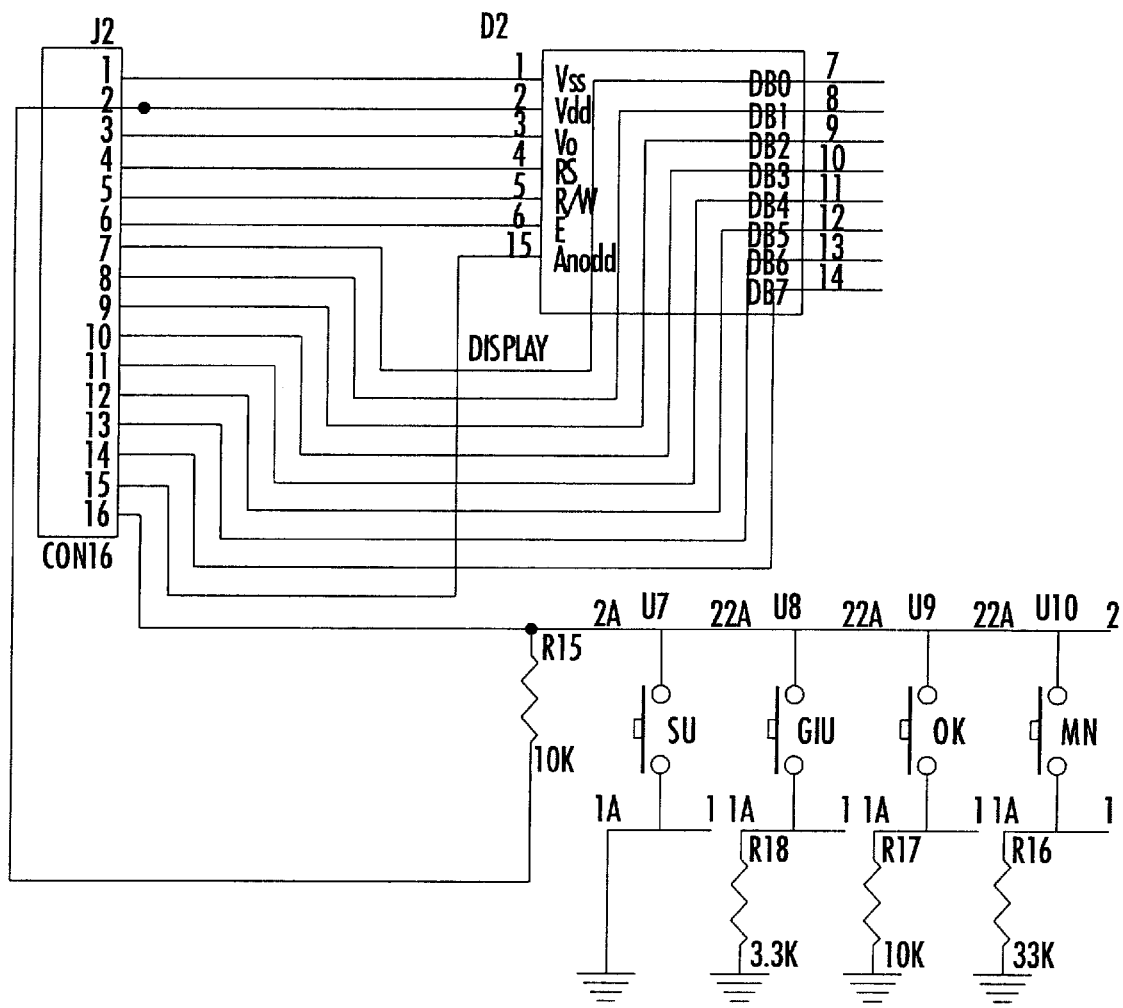

A circuit scheme of the memory control unit MCU of the amplifier and of the filter, using the commercial device ST52_420, is depicted in FIG. 10. A circuit implementation of the memory having a parallel communication port is depicted in FIG. 11. A sample realization of the circuits for driving and controlling the motor are shown in FIG. 12. A circuit implementation of the display and of the four-key keyboard is shown in FIG. 13.

The pressure Holter of the invention has proven itself to be very reliable. The use of the fuzzy logic processing in the Holter is very effective because of the need to evaluate factors that are not easily quantifiable (fuzzy), a processing of which may be greatly optimized by relying on fuzzy logic. Information relative to the current state of physical exertion of the patient permits "weighting" in a most appropriate way the pressure values measured by the Holter. This avoids improper alarms, for example, when relatively high pressure values are read in coincidence with a particularly intense physical activity.

Moreover, the instrument exploits the results of the measurements already carried out for evaluating the most appropriate time to carrying out the next measurement. In this way, the carrying out of repeated measurements of little significance can be avoided, thus preventing undue discomforts to the patient.

The instrument of the invention, besides representing an outstanding measurement and monitoring instrument, may also be used in medical research programs because of the possibility of downloading pressure readings and movement data stored throughout a full day. Therefore, it permits the building up a database of blood pressure data to be used in subsequent analyses, strictly for controlling a patient or for a broader range of clinical investigations, such as for studying the cycling of arterial pressure throughout the day.

That which is claimed is:

1. A blood pressure Holter system comprising:
   means for detecting and classifying movement of a user's body for producing an index of a state of physical exertion corresponding to maximum and minimum values of arterial pressure; and
   fuzzy logic means for processing the maximum and minimum values of arterial pressure using fuzzy logic.

2. A blood pressure Holter system according to claim 1, wherein the maximum and minimum values comprises systolic and diastolic values of the arterial pressure.

3. A blood pressure Holter system according to claim 1, further comprising an inflatable constriction sleeve worn on an arm of the user; and wherein said fuzzy logic means controls inflation and deflation of said constriction sleeve by repeatedly interrupting the inflation, reading an amplitude of arterial pulsations, comparing a current amplitude with an amplitude read and stored during a preceding step of the inflation, establishing duration of a next phase of inflation of said constriction sleeve and stopping the inflation upon detecting a progressive decrease of the amplitude of the arterial pulsations.

4. A blood pressure Holter system according to claim 1, further comprising an inflatable constriction sleeve worn on an arm of the user; and wherein said fuzzy logic means controls deflation of said constriction sleeve by reading an amplitude of arterial pulsations, comparing the amplitude of a current pulsation with an amplitude read and stored before, and recording a maximum arterial pressure upon detecting a maximum gradient of increment of the amplitude of the arterial pulsations and successively registering a minimum arterial pressure corresponding to a detected minimum gradient of decrement of the amplitude of the arterial pulsations during release of an internal pressure of said constriction sleeve.

5. A blood pressure Holter system according to claim 1, further comprising:
   an inflatable constriction sleeve worn on an arm of the user and comprising a first sensor for sensing internal air pressure thereof corresponding to the maximum and minimum values of arterial pressure; and
   a second sensor carried adjacent a chest of the user for sensing movement of the user's body.

6. A blood pressure Holter system according to claim 5, wherein said means for detecting and classifying comprises:
   an analog/digital conversion circuit for converting a first analog signal generated by said first sensor and a second analog signal generated by said second sensor into corresponding digital data sequences each including motion parameters;
   fuzzy logic labeling means for labeling and processing the respective motion parameters;
   a memory for storing at least one of the labels and processed respective motion parameters; and
   fuzzy logic classification means for classifying activity of the user as a function of the labels.

7. A blood pressure Holter system according to claim 6, wherein activity of the user is classified as either calm, normal or restless.

8. A blood pressure Holter system comprising:
   a device for acquiring systolic and diastolic values of arterial pressure of a user;
   a detection and classification circuit for detecting and classifying movement of the user's body for producing an index of a state of physical exertion corresponding to the systolic and diastolic values of arterial pressure; and
   a fuzzy logic circuit for processing the systolic and diastolic values of arterial pressure using fuzzy logic.

9. A blood pressure Holter system according to claim 8, wherein said device comprises an inflatable constriction sleeve worn on an arm of the user and comprises a first sensor for sensing internal air pressure thereof corresponding to the systolic and diastolic values of arterial pressure; and the system further comprises a second sensor carried adjacent a chest of the user for sensing movement of the user's body.

10. A blood pressure Holter system according to claim 8, wherein said device comprises an inflatable constriction sleeve worn on an arm of the user; and wherein said fuzzy logic circuit controls inflation and deflation of said constriction sleeve by repeatedly interrupting the inflation, reading an amplitude of arterial pulsations, comparing a current amplitude with an amplitude read and stored during a preceding step of the inflation, establishing duration of a next phase of inflation of said constriction sleeve and stopping the inflation upon detecting a progressive decrease of the amplitude of the arterial pulsations.

11. A blood pressure Holter system according to claim 8, wherein said detection and classification circuit comprises:
   an analog/digital conversion circuit for converting a first analog signal generated by said first sensor and a second analog signal generated by said second sensor into corresponding digital data sequences each including motion parameters;
   a fuzzy logic labeling circuit for labeling and processing the respective motion parameters;
   a memory for storing at least one of the labels and processed respective motion parameters; and
   a fuzzy logic classification circuit for classifying activity of the user as a function of the labels.

12. A blood pressure Holter system according to claim 11, wherein activity of the user is classified as either calm, normal or restless.

13. A blood pressure Holter system according to claim 8, wherein said device comprises an inflatable constriction sleeve worn on an arm of the user; and wherein said fuzzy logic circuit controls deflation of said constriction sleeve by reading an amplitude of arterial pulsations, comparing the amplitude of a current pulsation with an amplitude read and stored before, and recording a high arterial pressure upon detecting a high gradient of increment of the amplitude of the arterial pulsations and successively registering a low arterial pressure corresponding to a detected low gradient of decrement of the amplitude of the arterial pulsations during release of an internal pressure of said constriction sleeve.

14. A blood pressure Holter system according to claim 13, wherein the high gradient of increment comprises a maximum gradient of increment and the low gradient of increment comprises a minimum gradient of increment.

15. A blood pressure Holter system comprising:
   an inflatable constriction sleeve worn on an arm of a user and comprising a first sensor for sensing internal air pressure thereof corresponding to systolic and diastolic values of arterial pressure;
   a second sensor carried adjacent a chest of the user for sensing movement of the user's body;
   a detection and classification circuit for detecting and classifying movement of the user s body for producing an index of a state of physical exertion corresponding to the systolic and diastolic values of arterial pressure; and
   a fuzzy logic circuit for processing the systolic and diastolic values of arterial pressure using fuzzy logic.

16. A blood pressure Holter system according to claim 15, wherein said device comprises an inflatable constriction sleeve worn on an arm of the user; and wherein said fuzzy logic circuit controls inflation and deflation of said constriction sleeve by repeatedly interrupting the inflation, reading an amplitude of arterial pulsations, comparing a current amplitude with an amplitude read and stored during a preceding step of the inflation, establishing duration of a next phase of inflation of said constriction sleeve and stopping the inflation upon detecting a progressive decrease of the amplitude of the arterial pulsations.

17. A blood pressure Holter system according to claim 15, wherein said detection and classification circuit comprises:
   an analog/digital conversion circuit for converting a first analog signal generated by said first sensor and a second analog signal generated by said second sensor into corresponding digital data sequences each including motion parameters;
   a fuzzy logic labeling circuit for labeling and processing the respective motion parameters;
   a memory for storing at least one of the labels and processed respective motion parameters; and
   a fuzzy logic classification circuit for classifying activity of the user as a function of the labels.

18. A blood pressure Holter system according to claim 17, wherein activity of the user is classified as either calm, normal or restless.

19. A blood pressure Holter system according to claim 15, wherein said device comprises an inflatable constriction sleeve worn on an arm of the user; and wherein said fuzzy logic circuit controls deflation of said constriction sleeve by reading an amplitude of arterial pulsations, comparing the amplitude of a current pulsation with an amplitude read and stored before, and recording a high arterial pressure upon detecting a high gradient of increment of the amplitude of the arterial pulsations and successively registering a low arterial pressure corresponding to a detected low gradient of decrement of the amplitude of the arterial pulsations during release of an internal pressure of said constriction sleeve.

20. A blood pressure Holter system according to claim 19, wherein the high gradient of increment comprises a maximum gradient of increment and the low gradient of increment comprises a minimum gradient of increment.

21. A method for monitoring blood pressure of a user while conducting daily activities, the method comprising:
   detecting and classifying movement of the user's body for producing an index of a state of physical exertion corresponding to systolic and diastolic values of arterial pressure; and
   processing the systolic and diastolic values of arterial pressure using fuzzy logic.

22. A method according to claim 21, wherein an inflatable constriction sleeve is worn on an arm of the user; and wherein the processing includes controlling inflation and deflation of the constriction sleeve by repeatedly interrupting the inflation, reading an amplitude of arterial pulsations, comparing a current amplitude with an amplitude read and stored during a preceding step of the inflation, establishing duration of a next phase of inflation of the constriction sleeve and stopping the inflation upon detecting a progressive decrease of the amplitude of the arterial pulsations.

23. A method according to claim 21, wherein an inflatable constriction sleeve is worn on an arm of the user; and wherein the processing includes controlling deflation of the constriction sleeve by reading an amplitude of arterial pulsations, comparing the amplitude of a current pulsation with an amplitude read and stored before, and recording a high arterial pressure upon detecting a high gradient of increment of the amplitude of the arterial pulsations and successively registering a low arterial pressure in coincidence with a detected low gradient of decrement of the amplitude of the arterial pulsations during release of an internal pressure of the constriction sleeve.

24. A method according to claim 23, wherein the high gradient of increment comprises a maximum gradient of increment and the low gradient of increment comprises a minimum gradient of increment.

25. A method according to claim 21, further comprising:

acquiring the systolic and diastolic values of arterial pressure using an inflatable constriction sleeve worn on an arm of the user and comprising a first sensor for sensing internal air pressure thereof corresponding to the systolic and diastolic values of arterial pressure; and sensing movement of the user's body using a second sensor carried adjacent a chest of the user.

26. A method according to claim 25, wherein detecting and classifying comprises:

converting a first analog signal generated by the first sensor and a second analog signal generated by said second sensor into corresponding digital data sequences each including motion parameters;

labeling and processing the respective motion parameters;

storing at least one of the labels and processed respective motion parameters in a memory; and classifying activity of the user as a function of the labels.

27. A method according to claim 26, wherein activity of the user is classified as either calm, normal or restless.

* * * * *